(12) United States Patent
Meyer

(10) Patent No.: US 6,433,015 B1
(45) Date of Patent: *Aug. 13, 2002

(54) METHOD FOR REDUCING BODY WEIGHT

(75) Inventor: Hans Meyer, Riehen (CH)

(73) Assignee: IPR-Institute for Pharmaceutical Research AG, Riehen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/446,865

(22) PCT Filed: Jun. 23, 1998

(86) PCT No.: PCT/CH98/00273

§ 371 (c)(1),
(2), (4) Date: Dec. 23, 1999

(87) PCT Pub. No.: WO99/00122

PCT Pub. Date: Jan. 7, 1999

(30) Foreign Application Priority Data

Jun. 25, 1997 (EP) .............................. 97110340

(51) Int. Cl.$^7$ ............................................. A61K 31/195
(52) U.S. Cl. ..................................................... 514/565
(58) Field of Search ................................. 514/561, 565

(56) References Cited

U.S. PATENT DOCUMENTS

| | | | | |
|---|---|---|---|---|
| 5,321,030 A | * | 6/1994 | Kaddurah-Daouk et al. | 514/275 |
| 5,324,731 A | * | 6/1994 | Kaddurah-Daouk et al. | 514/275 |
| 5,998,457 A | * | 12/1999 | Kaddurah-Daouk | 514/392 |
| 6,114,379 A | * | 9/2000 | Wheelwright et al. | 514/492 |

FOREIGN PATENT DOCUMENTS

| | | | |
|---|---|---|---|
| WO | 9009192 | * | 8/1990 |
| WO | 9208456 | * | 5/1992 |

* cited by examiner

*Primary Examiner*—William R. A. Jarvis
*Assistant Examiner*—Vickie Kim
(74) *Attorney, Agent, or Firm*—Pennie & Edmonds LLP

(57) ABSTRACT

A process for reducing the body weight of overweight humans and domestic animals, such as dogs and cats, by administering creatine is provided. Creatine is administered at a daily dose of 0.15 mg–15 mg per kilogram of body weight by various methods, including oral administration, injection, infusion, and suppositories for rectal application. Also provided is the use of creatine for manufacturing a medicament containing creatine that can be administered by the process of the invention.

12 Claims, 1 Drawing Sheet

METHOD FOR REDUCING BODY WEIGHT

INTRODUCTION

The present invention concerns a process for reduction of the body weight of overweight humans and domestic animals by administration of creatine as well as the use of creatine for the manufacture of a medicament for use in this process.

BACKGROUND OF THE INVENTION

Overweight of humans and domestic animals is very common today, particularly in industrial countries. For instance, in the industrial countries, every second to third person is overweight. Overweight constitutes a considerable health hazard and very often leads to secondary diseases such as high blood pressure, arteriosclerosis, diabetes and diseases of the joints. The treatment with medicaments such as appetite depressants is very often accompanied by health hazards and unpleasant side effects and therefore unsatisfactory. There is therefore a need for a process with which the desirable weight reduction can be attained without the side effects and hazards connected with the use of centrally active appetite depressants.

Creatine [N-Amidinosarcosine; N-Carbamimidoyl-N-methylglycine; N-Aminoiminomethyl-N-methylglycine] is a natural substance predominantly present in muscle tissue of the vertebrates. Minor amounts are contained in the blood and brain. In the muscle, the greater part of creatine is present as creatine phosphate. Creatine phosphate plays an important role in the muscle as energy storage. In the working muscle, creatine phosphate with adenosine diphosphate (ADP) under the influence of the enzyme creatine kinase yields adenosine triphosphate (ATP) and creatine. In the resting muscle the reaction proceeds in the reverse direction. Intensive muscle contractions lead to exhaustion of the creatine phosphate depots and therewith to the known conditions of fatigue. Creatine is not synthesized in the muscle, it is transported into the muscle via the blood stream, partly after synthesis in the liver and pancreas and back resorption in the kidney, partly after food intake. Creatine is excreted via the kidney as creatinine.

From WO 94/02127 it is known that administration of creatine in a daily dosage of at least 15 g to 30 g, corresponding to 0.2 g to 0.4 g per kilogram of the body weight, in physically active test persons, e.g. athletes, leads to an enhancement of body weight, wich results from an increase of muscle mass. The same effect of creatine is described by R. Sahelian in "Creatine, Nature's Muscle Builder", page 28, Avery Publishing Group, New York (1997) and by G. Gremion in the publication, "Läufer" (1995), 8, pages 39–40. In these publications is additionally mentioned that beside an increase of the muscle mass the fat mass is decreased, but finally always an increase of body weight results.

However, the influence on body weight through creatine in the sense of a weight increase depending on an increase of muscle mass with simultaneous reduction of fat mass described in the above literature, only appears together with simultaneous high muscle strain, i.e. e.g. in athletes who are in tough performance training. An influencing of body weight by taking creatine without simultaneous strong muscular strain has hitherto not been described.

DETAILED DESCRIPTION OF THE INVENTION

Figure 1:
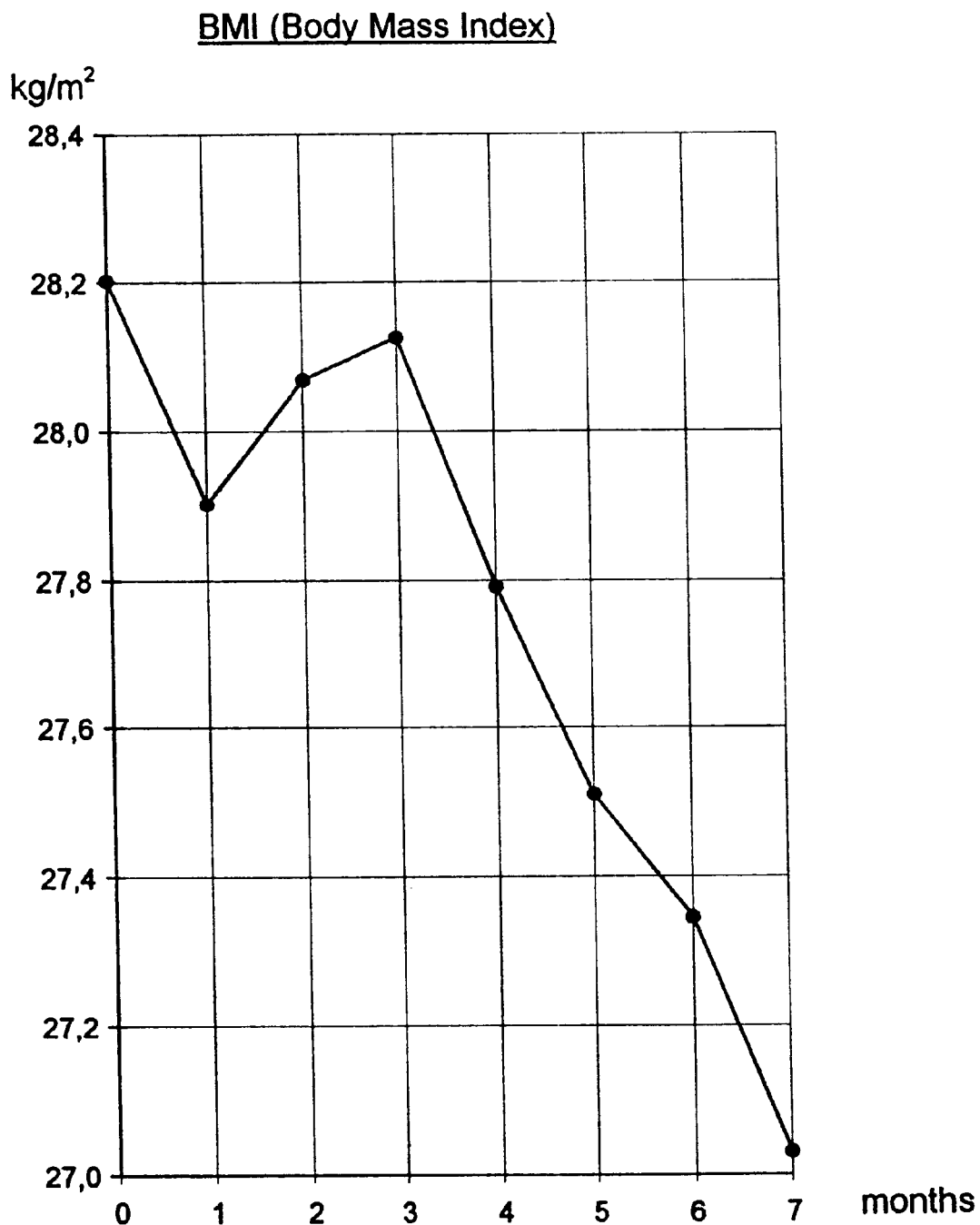
FIG. 1 shows the result of seven (7)-month study on body weight loss in 22 subjects who were administered with creatine at a daily dosage of 100–600 mg.

It has now been found that the body weight of overweight persons and overweight domestic animals can be reduced by administering a daily dosage of 0.15 mg to 15 mg of creatine per kilogram body weight.

Subject of the present invention is therefore a process for reduction of the body weight of overweight persons and overweight domestic animals which is characterized in that the overweight persons and overweight domestic animals are administered daily 0.15 mg to 15 mg of creatine per kilogram body weight. This dosage corresponds in a person of about 70 kg body weight the intake of 10 mg to 1000 mg of creatine per day. Preferably the daily dosage amounts to 1 mg to 5 mg of creatine per kilogram body weight or in a person of about 70 kg body weight correspondingly daily 50 mg to 300 mg of creatine. Particularly preferred is a daily dosage of creatine of 1.5 mg/kg body weight, corresponding to 100 mg of creatine daily in person with a body weight of about 70 kg. The daily dosage of creatine is preferably taken as a single dose in the morning, but it can also be divided up in two or more partial dosages.

The expression creatine used in the present description also comprises creatine phosphate.

As domestic animals in particular cats and dogs come into consideration.

A further subject of the present invention is the use of creatine in a process for the manufacture of a medicament for use in a process for reduction of the body weight of overweight persons and domestic animals, which is characterized in that the overweight persons and domestic animals are administered a daily dosage of 0.15 mg to 15 mg of creatine per kilogram body weight.

According to one embodiment of the present invention creatine can also be used in combination with vitamins, trace elements and/or electrolytes. As vitamins all fat- and water-soluble vitamins are suitable. Suitable trace elements are for example iron, fluorine, iodine, copper, lithium, manganese, molybdenum, nickel, selenium, silicium, vanadium, tin and zinc. Suitable electrolytes are for example electrolytes of the water balance such as $Na^+$, $K^+ Mg^{2+}$, $Ca^{2+}$, $Mn^{2+}$, $Zn^{2+}$, $Cl^-$, $SO_4^{2-}$ and $PO_4^{3-}$.

Moreover, creatine can also be combined with other slimming agents (anti-adipositas). Since creatine is an endogenic substance, no side effects appear in the low dosages employed according to the invention and patient compliance is therefore excellent. A considerable advantage of the process of the invention for reduction of the body weight consists in the fact that the eating habits can be maintained and that daily only one tablet has to be taken.

The use of creatine for the manufacture of medicaments according to the invention comprises its addition into all administration forms suitable for the above mentioned field of use. Such administration forms are e.g. tablets, dragees, capsules or other solid medicaments disintegrating in the gastric juice, mono- or multilayered solid medicaments ensuring a delayed or stepwise release of the active ingredient, pellets in capsules or pressed with immediate or delayed release, solid medicaments resistant to gastric juice, solutions or suspensions of the active substance in soft gelatine capsules or hard gelatine capsules or other wrappings sealed according to specific methods, forms soluble or suspendible in water or other beverages such as e.g. effervescent tablets, effervescent granulates, soluble tablets and soluble granulates, liquid medicaments such as drops or syrups for taking as concentrate or diluted in water or other beverages, preparations for transdermal application such as e.g. plasters, gels, creams and salves, liquid administration forms for injection and infusion, suppositories for rectal application.

Preferred are solid administration forms such as tablets, dragees, capsules, granulates, suppositories and liquid forms such as solutions or suspensions.

In overweight domestic animals the oral administration forms are preferably mixed with the feed or the drinking water.

The manufacture of the medicament is characterized in that creatine is mixed with physiologically acceptable auxiliary substances in a manner known per se and brought into an administration form suitable for the use by pressing, granulating, filling into capsules or adding to salve bases.

In the manufacture of the medicament conventional processes for admixture, granulation, drageeing, dissolution or lyophilization can be employed.

Medicaments for oral use are obtained e.g. by combining the active ingredient with solid carrier substances, the mixture obtained is, if desired, granulated and the mixture or granulate is, if desired or necessary, after the addition of suitable auxiliary substances, processed to tablets or dragee cores.

Suitable carrier substances are in particular filling substances such as sugars, e.g. lactose, saccharose, mannitol or sorbitol, cellulose preparations and/or calcium phosphates, e.g. tricalcium phosphate or calcium hydrogen phosphate, moreover thickening agents such as starch paste using e.g. maize-, wheat-, rice- or potatostarch, gelatine, tragacanth gum, methyl cellulose, hydroxypropylmethyl cellulose, sodium carboxy methyl cellulose and/or polyvinyl pyrrolidone and/or, if desired, disintegrating agents such as the above mentioned starches, moreover carboxymethyl starch, cross-meshed polyvinyl pyrrolidone, agar, alginic acid or a salt thereof, such as sodium alginate. As auxiliary agents primarily flow regulation agents and lubricants are suitable such as e.g. silicic acid, silicone dioxide, talcum, stearic acid or salts thereof such as magnesium or calcium stearate and/or polyethylene glycol.

Further orally useful medicaments are hard, two-piece gelatine capsules as well as soft closed capsules made of gelatine and a softener such as glycerol or sorbitol. The hard capsules can contain the active ingredient in the form of a granulate, for instance in admixture with filling substances such as lactose, thickening agents such as starches and/or flowing agents such as talcum or magnesium stearate and, if desired, stabilizing agents. In soft capsules the active substance is preferably dissolved or dispersed in suitable liquids such as fatty oils, paraffin oil or liquid polyethylene glycol, stabilizing agents optionally being added.

For parenteral administration primarily aqueous solutions are useful, moreover suspensions of the active substance, such as corresponding oily injection suspensions; suitable lipophilic solvents or vehicles being used, such as fatty oils, e.g. sesame oil, or fatty acid esters, such as e.g. ethyl oleate or triglycerides, or aqueous injection suspensions which contain viscosity increasing substances, e.g. sodium carboxymethyl cellulose, sorbitol and/or dextrane and optionally also stabilizing agents.

The contents of active ingredient in the medicament can e.g. amount to from 0.1 to 99 per cent by weight of the preparation, preferably 1 to 90 per cent by weight.

EXAMPLES

The present invention is illustrated further by the following examples.

[Creatine-monohydrate (Chemie Linz, A), Avicel PH 102 (microcrystalline cellulose; FMC Corp.), Explotab (sodium starch glycolate; Mendell, Patterson, New York), Kollidon K30 (polyvinyl pyrrolidone or polyvidone or PVP; BASF, U.K.), Syloid 244 (silica gel; W. R. GracelDavison Chemical Div., Baltimore), Cutina HR (wax mixture, ethoxylated esters; Henkel) are commercial products.]

Example 1

Tablets

Tablets containing 100 mg of creatine can be manufactured as follows:

| Composition for | 1 tablet | 1000 tablets |
|---|---|---|
| Creatine monohydrate | 100,00 mg | 100,00 g |
| Avicel PH 102 | 17,20 mg | 17,20 g |
| Explotab | 10,12 mg | 10,12 g |
| Kollidon K30 | 6,00 mg | 6,00 g |
| Syloid 244 | 0,64 mg | 0,64 g |
| Cutina HR | 1,04 mg | 1,04 g |

Creatine, Avicel and Explotab are homogenously mixed within ten minutes, rubbed through a sieve (710 $\mu$m) and mixed agein. The Kollidon is added as 20 percent solution, the mixture well mixed and subsequently rubbed through a sieve (710 $\mu$m). The moist granulate is dried 5 hours at 45° C. in a drying cabinet and sieved again (710 $\mu$m). Syloid and Cutina are homogenously mixed, sieved (710 $\mu$m) and homogenously mixed with the dry granulate. The finished granulate is pressed to tablets on the tabletting machine with a stamp of 6 mm diameter. (Tablet weight: 135 mg).

Example 2

Granulate

A granulate containing 1.0 g of creatine per 1.33 g of granulate can be manufactured as follows:

Composition for 1330 g of granulate:

| Creatine | 1000 g |
|---|---|
| Avicel PH 102 | 170 g |
| Explotab | 100 g |
| Kollidon K30 | 60 g |

Creatine, Avicel and Explotab are homogenously mixed for 10 minutes, rubbed through a sieve (710 $\mu$m) and mixed again. After the addition of the Kollidon as 20 percent aquid solution the mixture is well stirred and subsequently rubbed through a sieve (710 $\mu$m). The moist granulate obtained is dried 5 hours at 45° C. in a drying cabinet and sieved agein (710 $\mu$m).

Use Example

An experiment was carried out with 22 test persons in order to confirm the weight reducing effect of creatine using the dosage according to the invention. The test persons were instructed for the duration of the experiment not to change their day-to-day habits (diet and physical exercise). In order to find the optimal dosage the test persons were initially divided into three groups with a daily dosage of either 100 mg, 300 mg or 600 mg of creatine. After 3 months the group with 100 mg had shown the most noticeable weight loss, whence the dosage was reduced in all test persons to a single dose of 100 mg. The results of the 7-month study are summarized in the following diagram. They demonstrate that after the 3 months dosage-finding period a steady decrease of body weight occured. The data are reported as so-called body mass index (BMI), which is calculated from the body weight in dilograms divided by the height in meters in square.

What is claimed is:

1. A process for reducing a body weight of a person or a domestic animal in need thereof, comprising:
   administering creatine to the person or domestic animal at a daily dosage of from about 0.15 mg/kg to about 5.0 mg/kg body weight.

2. The process according to claim 1, wherein the daily dosage is from about 1 mg/kg to about 5 mg/kg body weight.

3. The process according to claim 1, wherein the daily dosage is about 1.5 mg/kg body weight.

4. The process according to claim 1, 2, or 3, wherein creatine is creatine phosphate.

5. The process of claims 1 or 2, wherein the creatine is administered in a solid dosage form.

6. The process of claims 1 or 2, wherein the creatine is administered in a liquid dosage form.

7. The process of claims 1 or 2, wherein the creatine is administered via oral route.

8. The process of claims 1 or 2, wherein the creatine is administered via tanadermal route.

9. The process of claims 1 or 2, wherein the creatine is in a gel form.

10. The process of claims 1 or 2, wherein the creatine in a beverage.

11. The process of claims 1 or 2, wherein the creatine is in a gum.

12. The process of claims 1 or 2, wherein the creatine is in a suppository.

* * * * *